United States Patent
Drobe

(10) Patent No.: US 9,675,242 B2
(45) Date of Patent: Jun. 13, 2017

(54) METHOD AND DEVICE FOR SCREENING A STATE OF OPHTHALMIC FATIGUE OF AN INDIVIDUAL

(71) Applicant: ESSILOR INTERNATIONAL (COMPAGNIE GENERALE D'OPTIQUE), Charenton le Pont (FR)

(72) Inventor: Bjorn Drobe, Singapour (SG)

(73) Assignee: ESSILOR INTERNATIONAL (COMPAGNIE GENERALE D'OPTIQUE), Charenton-le-Pont (FR)

(*) Notice: Subject to any disclaimer, the term of this patent is extended or adjusted under 35 U.S.C. 154(b) by 51 days.

(21) Appl. No.: 14/417,981

(22) PCT Filed: Jul. 25, 2013

(86) PCT No.: PCT/FR2013/051799
§ 371 (c)(1),
(2) Date: Jan. 28, 2015

(87) PCT Pub. No.: WO2014/023889
PCT Pub. Date: Feb. 13, 2014

(65) Prior Publication Data
US 2015/0164315 A1    Jun. 18, 2015

(30) Foreign Application Priority Data
Aug. 9, 2012  (FR) .................... 12 02219

(51) Int. Cl.
*A61B 3/02* (2006.01)
*A61B 3/00* (2006.01)
*A61B 3/09* (2006.01)
*A61B 3/032* (2006.01)

(52) U.S. Cl.
CPC ............. *A61B 3/09* (2013.01); *A61B 3/032* (2013.01)

(58) Field of Classification Search
USPC ............................................. 351/239, 246
See application file for complete search history.

(56) References Cited

U.S. PATENT DOCUMENTS

| 698,833 A | 4/1902 | Hardy |
|---|---|---|
| 7,393,102 B2 | 7/2008 | Horie |
| 2006/0103808 A1 | 5/2006 | Horie |

FOREIGN PATENT DOCUMENTS

FR    2 880 789 A    7/2006

OTHER PUBLICATIONS

International Search Report dated Nov. 22, 2013, in corresponding PCT application.

*Primary Examiner* — Jack Dinh
(74) *Attorney, Agent, or Firm* — Young & Thompson

(57) ABSTRACT

A method of screening a state of ophthalmic fatigue of an individual, includes steps: a1) of positioning a target (120) in relation to the individual in such a way that the target is visible by at least one of the two eyes of the individual, a2) of assessment by the individual of the sharpness of the target, and a3) of deducing a state of ophthalmic fatigue of the individual depending on whether the target is seen by the individual in a sharp or blurred manner. According to the invention, prior to step a2), there is provision for a step a0) of adjusting the size of the target and/or the position of the target in relation to the individual, as a function of the age of the individual.

14 Claims, 2 Drawing Sheets

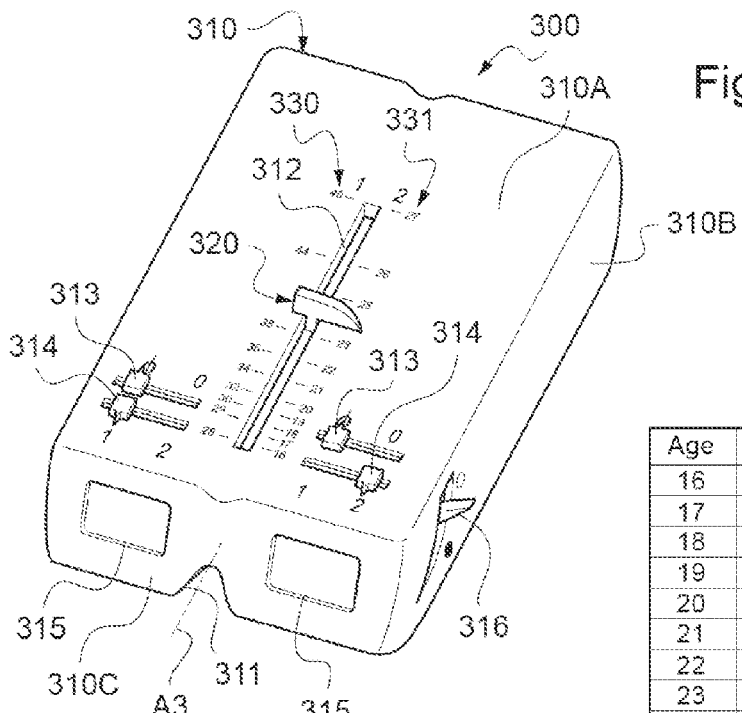
Fig.4
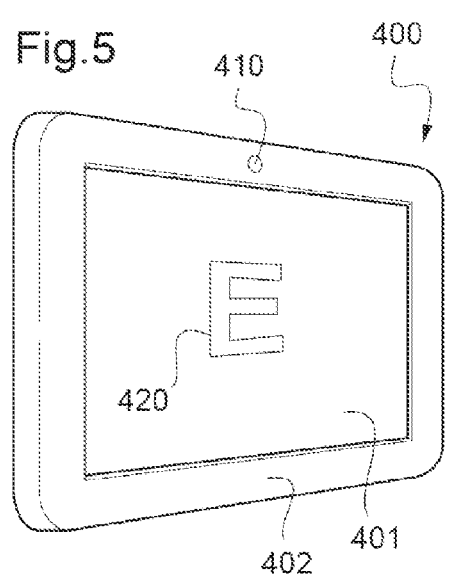
Fig.5
Fig.6
| Age | D_age | +1.5 δ | -5 δ |
|---|---|---|---|
| 16 | 7.6 | 6.8 | 12.2 |
| 17 | 7.8 | 7.0 | 12.8 |
| 18 | 8.0 | 7.1 | 13.3 |
| 19 | 8.2 | 7.3 | 14.0 |
| 20 | 8.5 | 7.5 | 14.6 |
| 21 | 8.7 | 7.7 | 15.4 |
| 22 | 9.0 | 7.9 | 16.2 |
| 23 | 9.2 | 8.1 | 17.1 |
| 24 | 9.5 | 8.3 | 18.2 |
| 25 | 9.8 | 8.6 | 19.4 |
| 26 | 10.2 | 8.8 | 20.7 |
| 27 | 10.5 | 9.1 | 22.2 |
| 28 | 10.9 | 9.4 | 24.0 |
| 29 | 11.3 | 9.7 | 26.1 |
| 30 | 11.8 | 10.0 | 28.6 |
| 31 | 12.2 | 10.3 | 31.6 |
| 32 | 12.8 | 10.7 | 35.3 |
| 33 | 13.3 | 11.1 | 40.0 |
| 34 | 14.0 | 11.5 | 46.2 |
| 35 | 14.6 | 12.0 | 54.5 |
| 36 | 15.4 | 12.5 | 66.7 |
| 37 | 16.2 | 13.0 | 85.7 |
| 38 | 17.1 | 13.6 | 120.0 |
| 39 | 18.2 | 14.3 | 200.0 |
| 40 | 19.4 | 15.0 | 600.0 |
| 41 | 20.7 | 15.8 | |
| 42 | 22.2 | 16.7 | |
| 43 | 24.0 | 17.6 | |
| 44 | 26.1 | 18.8 | |
| 45 | 28.6 | 20.0 | |
| 46 | 31.6 | 21.4 | |
| 47 | 35.3 | 23.1 | |
| 48 | 40.0 | 25.0 | |
| 49 | 46.2 | 27.3 | |
| 50 | 54.5 | 30.0 | |

METHOD AND DEVICE FOR SCREENING A STATE OF OPHTHALMIC FATIGUE OF AN INDIVIDUAL

TECHNICAL FIELD OF THE INVENTION

Generally, the present invention relates to methods for diagnosing the ophthalmic accommodation of individuals.

It more particularly relates to a method for screening for a state of ophthalmic fatigue of an individual, comprising steps:

a1) of positioning a target relative to the individual in such a way that the target is visible by at least one of the two eyes of the individual;

a2) of appraisal by the individual of the clearness of the target; and a3) of deducing a state of ophthalmic fatigue of the individual depending on whether the target is seen clearly or hazily by the individual.

It also relates to a device for screening for a state of ophthalmic fatigue of an individual, comprising:

a carrier comprising a bearing portion to be applied against the face of an individual and a slide rail;

a target slidably mounted in the slide rail of the carrier; and at least one graduation located along the slide rail for pinpointing the position of the target in the slide rail.

PRIOR ART

Accommodation is defined as the automatic and involuntary action of ciliary muscles to deform the eye so it can clearly see objects located at various distances.

More precisely, during accommodation, the curvature of the crystalline lens changes under the influence of ciliary muscles, thereby allowing clear images to be formed on the retina. The crystalline lens flattens for clear vision of far-off objects and becomes more rounded to focus on nearby objects.

The minimum accommodation distance of a given individual is then defined as the distance from which this individual may see an object perfectly clearly. Below this minimum accommodation distance, the ciliary muscles are not able to sufficiently round the crystalline lens to allow clear images to be formed on the retina.

It is known that this minimum accommodation distance increases with age, and that it increases more or less rapidly from one individual to another. It also increases when an individual is tired.

It is known to measure this minimum accommodation distance using an ophthalmic rule more commonly known as the "RAF rule" (for Royal Air Force rule).

This ophthalmic rule comprises, on the one hand, a metal rod graduated in diopters and in meters, one end of which forms a fork to be applied against the face of the wearer, and, on the other hand, a target mounted so as to be translationally movable over the metal rod.

The way in which this rule is used consists in positioning the target on the rod opposite the fork, then in applying this fork to the face of the individual while maintaining the metal rod on the axis of the eyes of the individual, and lastly in gradually bringing the target closer to the individual until a limit position is reached level with which the individual no longer sees this target clearly.

The minimum accommodation distance may then be read directly from the graduation provided for this purpose.

However, the Applicant has noticed that the use of this ophthalmic rule generally results in measurements that are overestimated in the sense that the minimum accommodation distances measured are generally smaller than the actual minimum accommodation distances of wearers.

This leads to prescription errors insofar as a pair of spectacles is not prescribed to certain people who would however benefit from what are referred to as antifatigue spectacles.

SUBJECT OF THE INVENTION

In order to remedy the aforementioned drawback of the prior art, the present invention provides a novel method for diagnosing the state of ophthalmic fatigue of an individual, making it possible to determine with precision whether or not the individual requires antifatigue spectacles or a particular type of care (advice on lighting ergonomics, artificial tears for combating ocular dryness, etc.).

More particularly, the invention provides a screening method such as defined in the introduction, in which provision is made, prior to step a2), for a step a0) of adjusting the size of the target and/or the position of the target relative to the individual, depending on the age of the individual.

The Applicant has noticed that the measurement errors obtained with an RAF rule result from the fact that the target is gradually moved toward the eyes of the individual, which allows the ciliary muscles to gradually contract to a threshold beyond which they are capable of contracting instantaneously.

Thus, the present invention consists in no longer gradually moving the target toward the individual, but rather in setting the position and/or the size of the target to a given value, then, once the target has been set-up, in asking the individual to look at the target so that he may determine whether he can see it clearly.

The size and/or position of the target is thus preset, depending on the age of the individual, by virtue of data from statistical studies that allow the minimum accommodation distance that an individual is supposed to have at a given age, if he is not suffering from any particular ophthalmic problems, to be determined.

A few generalities on the subject of ophthalmic fatigue will now be recalled.

The minimum accommodation distance of an individual varies naturally with the age of an individual. This variation is not an ophthalmic fatigue since it is durable and irreversible.

Ophthalmic fatigue is in contrast a temporary and reversible state of fatigue of the ciliary muscles of an individual. It is a normal state that healthy individuals reach after their ciliary muscles have been solicited vigorously.

Thus, what the invention seeks to determine here does not concern the irreversible component of visual problems of the individual, but rather the occasional and non-pathological component of these problems.

Moreover, during implementation of the invention, it is not a question of comparing values measured for an individual with those of a healthy individual, but rather of comparing the values measured for an individual the ciliary muscles of whom are fatigued with those that would be measured for the same individual, for example just after he has woken up, when his ciliary muscles are rested.

Advantageously, if, in step a2), the target is seen to be hazy by the individual, provision is made following step a3) for steps:

b1) of enlarging the size of the target and/or of moving the target away from the individual by a preset distance;

b2) of appraisal by the individual of the clearness of the target; and b3) if, in step b2), the individual sees the target more clearly, of deducing a need for an antifatigue correction.

Correcting the size and/or position of the target thus makes it possible to check whether the accommodation defect observed is indeed due to a problem with ophthalmic fatigue that a pair of antifatigue spectacles could remedy, or indeed whether it is a question of a more serious problem (in which case the individual will have to undergo additional examinations).

The following are other advantageous and nonlimiting features of the method according to the invention:
- in step a0), only the distance between the target and the individual is adjusted;
- step b1) consists in inserting at least one corrective lens between the eye of the individual and the target;
- the corrective lens has a nonzero spherical power and/or a nonzero cylindrical power and/or a nonzero prismatic power and/or an antireflection coating and/or a tinted coating and/or is formed by a lens with a depth of field;
- in step a0), the distance between the target and the individual is adjusted also depending on the time of day at which the screening is carried out and/or on the geographical origin of the individual and/or on the clearness of the target and/or on the contrast of the target;
- in step a0), only the size of the target is adjusted;
- step b1) consists in enlarging the size of the target;
- prior to step a2), the individual is equipped with his customary corrective equipment (for example his customary pair of corrective spectacles or his customary contact lenses);
- steps a1) and a2) are carried out simultaneously or in succession on both eyes of the individual; and
- following step a3), provision is made for a step c1) of storing the state of ophthalmic fatigue deduced in step a3) in memory and of transmitting said state, via a computer network, to a remote location.

The invention also relates to a screening device such as defined in the introduction, in which said graduation indicates ages.

The following are other advantageous and nonlimiting features of the device according to the invention:
- the carrier comprises means for positioning a corrective lens, said means being located between the bearing portion and the target;
- provision is made for at least two age-indicating graduations and provision is made for means for positioning a scale-changing lens; and
- the target comprises at least one letter or image.

DETAILED DESCRIPTION OF AN EXAMPLE EMBODIMENT

The following description, given with regard to the appended drawings, which are given by way of nonlimiting example, will allow what the invention consists of and how it can be carried out to be understood.

In the appended drawings:

FIG. 4 is a schematic perspective view of a third embodiment of the screening device according to the invention;

FIG. 5 is a schematic perspective view of a fourth embodiment of the screening device, suitable for implementing a screening method according to the invention; and FIG. 6 is a table illustrating variations in minimal accommodation distance as a function of the age of individuals and the power of the scaling lens.

FIGS. 1, 3, 4 and 5 show four embodiments of a device 100; 200; 300; 400 for screening for a state of ophthalmic fatigue of an individual.

Ophthalmic fatigue (or "visual fatigue") is a reversible physiological effect resulting from the ocular muscles and the retina being excessively solicited in an attempt to preserve a clear image via ineffective adjustments. It is accompanied by a decrease in the ability to carry out a visual task and by a modification of the strategy used to accomplish this task; it is an alarm signal and treatment is recommended.

Ophthalmic fatigue may give rise not only to subjective symptoms and physiological modifications, but also to a decrease in visual performance.

Ophthalmic fatigue is more precisely studied in the document "*La fatigue visuelle*" published by the environmental physiology service of the INRS (Institut National de Recherche et de Sécurité) in March 1992.

In each of these four embodiments, the screening device 100; 200; 300; 400 is more precisely provided in order to make it easier for an optician to determine whether a patient has or does not have a good near vision and whether, thus, he does or does not require a pair of what are called antifatigue spectacles.

To do this, the screening device 100; 200; 300; 400 is provided in order to determine whether, given the age of the patient, each of the two eyes of the patient has a satisfactory "minimum accommodation distance".

The expression "minimum accommodation distance" is understood to mean the minimum distance at which an individual can see an object clearly.

Figure 1:
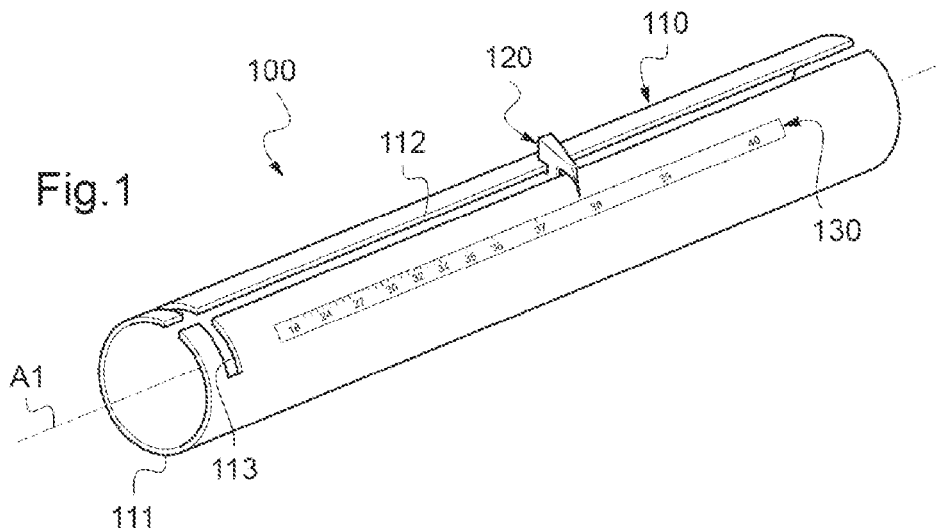
FIG. 1 is a schematic perspective view of a first embodiment of a screening device according to the invention.
Figure 3:
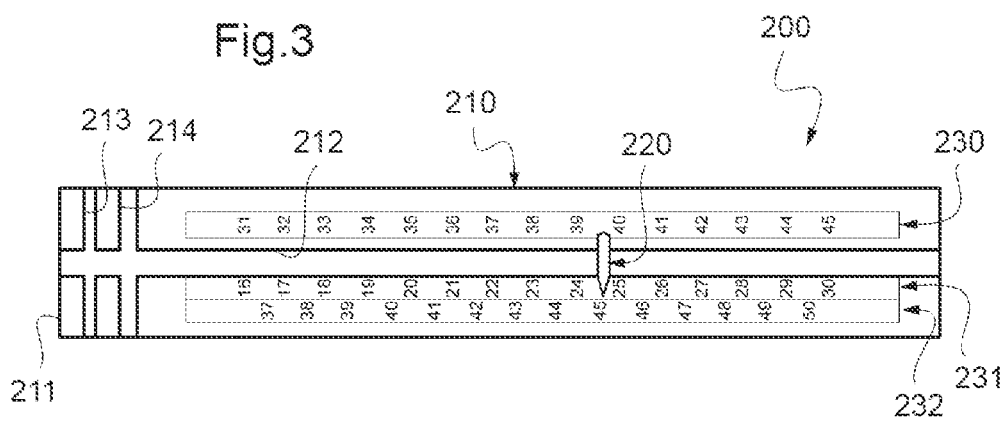
FIG. 3 is a schematic perspective view of a second embodiment of the screening device according to the invention.

In the three first embodiments shown in FIGS. 1, 3 and 4, respectively, the screening device 100; 200; 300 comprises:
- a carrier 110; 210; 310 comprising a bearing portion 111; 211; 311 to be applied against the face or the spectacles of the patient, and a slide rail 112; 212; 312;
- a target 120; 220; 320 slidably mounted in the slide rail 112; 212; 312 of the carrier 110; 210; 310; and
- at least one graduation 130; 230, 231, 232; 330, 331 located along the slide rail 112; 212; 312 for pinpointing the position of the target 120; 220; 320 in the slide rail 112; 212; 312.

According to one particularly advantageous feature of the screening device according to the invention, this graduation 130; 230, 231, 232; 330, 331 indicates ages.

According to one advantageous feature of this screening device, the carrier 110; 210; 310 furthermore comprises means 113; 213; 313 for positioning a corrective lens between the bearing portion 111; 211; 311 and the target 120; 220; 320, in order, if required, to make it easier to see the target.

These positioning means 113; 213; 313 are therefore designed to receive, if required, a corrective lens, so that the latter remains removable.

They will therefore possibly take various forms, provided that they allow the corrective lens to be positioned and extracted manually without using a tool.

The various embodiments of the screening device will be described in more detail below.

FIG. 1 shows the first embodiment of the screening device 100.

In this embodiment, the carrier 110 takes the form of a substantially cylindrical tube that is axisymmetric about a longitudinal axis A1.

This tubular carrier 110 here has a length of 30 centimeters, an inside diameter of 5 centimeters and an outside diameter of 5.4 centimeters.

It is a single part produced by molding a transparent plastic.

The bearing portion 111 of this tubular carrier 110, which portion 111 is intended to be applied against the face of the patient or against the pair of spectacles that the patient is wearing, is thus formed by one of the circular ends of this tubular carrier 110.

The slide rail 112 of this tubular carrier 110, in which rail 112 the target 120 slides, is for its part formed by a rectilinear longitudinal slit that extends all the way along the length of the tubular carrier 110, parallel to the longitudinal axis A1, and that here has a width of 5 millimeters.

Such as shown in FIG. 1, the graduation 130 which indicates ages is printed on a rectangular sticker that is adhesively bonded parallel to the slide rail 112, along the length of the latter.

This sticker has, like a ruler, two types of marks. First it has, along its edge adjacent to the slide rail 112, twenty-three short parallel lines that are spaced apart pairwise and of axes orthogonal to the longitudinal axis A1. It moreover has, opposite at least some of these lines, numbers indicating ages.

Each of the lines is associated with a given age, comprised between 18 and 40 years. The spacing between the lines increases from the bearing portion 111 to the opposite end of the tubular carrier 110.

Each of the ages noted on the graduation 130 indicates the age associated with the line opposite which it is located. The ages noted on the graduation 130 increase from the bearing portion 111 to the opposite end of the tubular carrier 110.

Each line is thus located a distance from the bearing portion 111 of the tubular carrier 110 that is substantially equal to the minimum accommodation distance an individual is supposed to have at a given age (that with which said line is associated), if he is not suffering from any particular ophthalmic problems.

This distance could be obtained by a statistical study carried out on a representative sample of individuals not suffering from any particular ophthalmic problems.

Here, this distance, denoted $D_{age}$, is calculated by means of the following mathematical formula:

$$D_{age}=1/(A_{age}-G), \text{ where:}$$

$A_{age}$ is the minimum accommodation distance (expressed in diopters) expected for an individual of given age; and G is a correction coefficient.

The minimum accommodation amplitude $A_{age}$ (or "least distance of distinct vision"), expressed in diopters, is calculated using the Hofsetter formula, according to which:

$$A_{age}=18.5-\tfrac{1}{3}\cdot age$$

The correction coefficient G is for its part here chosen to be equal to 0.

The result obtained is given, in millimeters, in the second column of the table in FIG. 6.

This correction coefficient G, which serves to modulate the threshold from which ophthalmic fatigue is diagnosed, could as a variant be chosen to be nonzero, for example in order to take into account an unclear or low-contrast target 120.

It could also be chosen to be nonzero in order to take into account the geographical zone in which the optician is working. Specifically, it has been observed that the minimum accommodation distance of an individual not suffering from any particular ophthalmic problems varies from one geographical zone to another.

Figure 2:
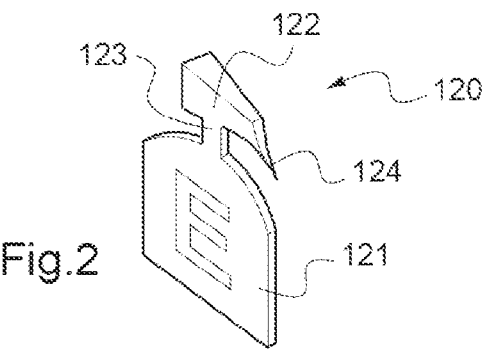
FIG. 2 is a schematic perspective view of the target of the screening device in FIG. 1.

The target 120, which is designed to slide along the slide rail 112, is for its part shown in more detail in FIG. 2.

It has a read portion 121, which comprises a pattern of any sort, a gripping portion 122 that can be easily handled by an optician in order to slide the target 120 along the slide rail 112, and a connecting portion 123 that connects the read portion 121 to the gripping portion 122.

The read portion 121 is housed in the interior of the tubular carrier 110 and it bears a pattern that is easily recognizable by the patient.

This read portion 121 here takes the form of a square plate, of side length of about 2 centimeters, the two main faces of which are oriented orthogonally to the longitudinal axis A1.

Its main face oriented toward the bearing portion 111 is that on which the pattern is printed.

This pattern is here formed by a letter (here an "E"). It could as a variant be formed by a drawing such as an animal, or by a set of letters of variable sizes.

Here, this pattern is black in color and is drawn on a white background. As a variant, provision could be made for the background to be a different color, for example green or red, and for the pattern to be another color.

The gripping portion 122 is for its part located on the exterior of the tubular carrier 110.

It takes the form of a rectangular plate, that here is coplanar with the read portion 121. As a variant, it could be offset relative to the read portion 121, in order to ensure a better grip.

Here it narrows at one of its two ends to a point 124 that allows, on the graduation 130, the age corresponding to the position of the target 120 along the slide rail 112 to be read with precision.

The connecting portion 123 for its part has a width, allowing for play, equal to the width of the slide rail 112 and a height, allowing for play, equal to the thickness of the tubular carrier 110, in order to allow the target 120 to be guided translationally along this slide rail 112.

As FIG. 1 shows, the positioning means that allow a corrective lens to be interposed between the bearing portion 111 of the tubular carrier 110 and the target 120, are here formed by a transverse slit 113.

This transverse slit 113 extends over half the periphery of the tubular carrier 110, on either side of the slide rail 112. It thus may receive, if required, any corrective lens when the optician so desires. The use of this lens will be described below.

Screening for a possible state of ophthalmic fatigue of the patient by means of this screening device 100 is then performed in the following way.

Beforehand, the optician asks the patient his age.

He then moreover asks him to put on his customary corrective equipment (for example his spectacles or contact lenses).

The optician then adjusts the position of the target 120 in the slide rail 112 such that its point 124 points to, on the graduation 130, the age indicated by the patient.

The optician then asks the patient to close one of his two eyes, for example his left eye.

He then positions the screening device 100 on the axis of the left eye of the patient, the bearing portion 111 making contact with the face or spectacles of the patient, such that when the latter opens his left eye, he can see the read portion 121 of the target 120.

The optician then asks the patient to judge the clearness of the letter printed on the target 120.

Depending on whether or not he is able to see the letter clearly, the optician deduces therefrom whether the patient presents a state of ophthalmic fatigue or not.

More precisely, if the patient judges the letter to be clear (for example if he is able to read the letter "E"), the optician deduces therefrom that the corresponding eye of the individual does not present a state of fatigue. The optician therefore deduces therefrom that the patient does not require, at least for his left eye, a pair of antifatigue spectacles.

In contrast, if the patient judges the letter to be somewhat unclear (for example if he is not able to read the letter "E"), the optician carries out an additional examination in order to check that it is only a state of fatigue that is affecting the left eye of the wearer (and that this visual problem is not more serious).

To do this, the optician places a corrective lens through the transverse slit 113 in the tubular carrier 110, the power of which is such that it allows a slight accommodation defect of the eye to be compensated for by artificially increasing the distance to and the size of the letter "E" seen by the patient.

The corrective lens used will preferably be a single-vision convergent lens, the spherical power of which will be strictly positive (for example equal to 0.6 diopters). It will also possibly be a lens with a depth of field.

As a variant, provision will possibly be made for this corrective lens to have a nonzero cylindrical power (alone or in combination with a spherical power) in order to correct possible cylindrical fatigue of the eye. Sphere-cylindrical correction is spoken of.

Whatever the type of this corrective lens, provision will moreover possibly be made for it to furthermore have an antireflection coating (in order to increase the contrast of the letter "E" on its background) and/or a tinted coating (in order to modify the color of the letter "E" and of its background).

In any case, once the corrective lens has been engaged in the transverse slit 113, the optician asks the patient whether he judges the letter to be clearer (for example whether he is able to read the letter "E" printed on the target 120).

If this is the case, the optician deduces therefrom that the patient requires a pair of antifatigue corrective spectacles.

In contrast, if this is not the case, the optician deduces therefrom that the patient is suffering from ophthalmic problems other than simple fatigue, and therefore advises the patient to visit an optometrist.

These operations are then carried out in the same way on the right eye of the patient.

According to one variant of this first embodiment, three minimum accommodation distances could be calculated for each age, namely:

a normal accommodation distance $D_2=1/(18.5-\frac{1}{3}\cdot age)$;

a maximum accommodation distance $D_1=1/(15-0.25\cdot age)$; and a minimum accommodation distance $D_3=1/(24-0.4\cdot age)$.

Three different scales of graduations may be obtained in this way, giving the optician a certain amount of freedom in the choice of the threshold from which ophthalmic fatigue is diagnosed.

FIG. 3 shows the second embodiment of the screening device 200.

In this embodiment, the carrier 210 has an almost identical shape to that of the carrier 110 shown in FIG. 1.

It thus has an end forming a bearing portion 211 to be pressed against the face or against the spectacles of the patient, and a slide rail 212 in which the target 220 slides, and a transverse slit 213 for receiving a corrective lens.

In the present case, the carrier 210 differs from the carrier 110 shown in FIG. 1 only in that it is smaller in length and comprises, parallel and in proximity to the transverse slit 213, between the bearing portion 211 and the target 220, a second transverse slit for receiving a scale-changing lens (the function of which will be described in detail below).

For its part, the target 220 has an identical shape to that of the target 120 shown in FIG. 2.

In this embodiment, provision is also made for three separate graduations 230, 231, 232.

Such as shown in FIG. 3, each graduation 230, 231, 232 is borne by a rectangular sticker on which only ages are printed.

Each sticker is adhesively bonded parallel to the slide rail 212 in proximity to the latter and a distance away from the other stickers.

The ages printed on the stickers are not the same. Thus, whatever its position in the slide rail 212, the target 220 points towards three different ages, depending on whether this age is read from one or other of the stickers.

It may thus be seen in FIG. 3 that one of the graduations 231 indicates ages comprised between 16 and 30 years, that another of the graduations 230 indicates ages comprised between 31 and 46 years, and that the last of the graduations 232 indicates ages comprised between 37 and 49 years.

The scales of these three graduations are therefore not the same. To pass from one graduation to another a scale-changing lens is used, which is placed for this purpose in said second transverse slit, between the eye of the patient and the target.

Using three graduations thus allows the length of the tubular carrier 210 to be decreased insofar as in order to indicate on one and the same graduation ages comprised between 18 and 49 years it would be necessary to provide a carrier of a length of about 50 centimeters.

Using three graduations also allows the precision of the measurements to be improved. Specifically, it may be seen, by comparing FIGS. 1 and 3, that the ages 18 and 19 years are spaced further apart on the graduation 231 in FIG. 3 than on the graduation 130 in FIG. 1, thereby making it easier to precisely place the target 220 opposite the desired age.

In the first set of markings 230, each printed age is located a distance from the bearing portion 211 of the tubular carrier 210 that is substantially equal to the minimum accommodation distance an individual is supposed to have at a given age, if he is not suffering from any particular ophthalmic problems. This distance, denoted $D_{age}$, is calculated by means of the aforementioned mathematical formula and is given, in millimeters, in the second column of the table in FIG. 6.

In the second and third set of markings 231, 232, each printed age is located at a distance from the bearing portion 211 of the tubular carrier 210 that is substantially equal to the minimum accommodation distance that an individual is supposed to have at a given age, if he is not suffering from any particular ophthalmic problems and if he is wearing a pair of spectacles equipped with lenses the spherical powers of which are either −5 diopters (graduation 231) or 1.5 diopters (graduation 232).

The distances calculated as a function of the age of the patient are given, in millimeters, in the fourth and third columns of the table in FIG. 6, respectively.

Thus, it will be understood that when no scaling lens is engaged in the second transverse slit 214, the graduation to be used by the optician to place the target 220 is the graduation 230 (opposite which the inscription "+0δ" appears). When a scaling lens of −5 diopters is engaged in the second transverse slit 214, the graduation to be used by the optician to place the target 220 is the graduation 231 (opposite which the inscription "−5δ" appears). When a scaling lens of +1.5 diopters is engaged in the second transverse slit 214, the graduation to be used by the optician to place the target 220 is the graduation 232 (opposite which the inscription "+1.5δ" appears).

Screening for the possible state of ophthalmic fatigue of the patient by means of this screening device 200 is then performed in substantially the same way as for the screening device 100 shown in FIG. 1.

The only difference is that:
- if the patient has an age comprised between 31 and 46 years, the optician must set the position of the target 220 using the graduation 230;
- if the patient has an age comprised between 18 and 31 years, the optician must engage in the second transverse slit 214 a scaling lens of −5 diopters and must set the position of the target 220 using the graduation 231; and
- if the patient has an age comprised between 47 and 49 years, the optician must engage in the second transverse slit 214 a scaling lens of +1.5 diopters and must set the position of the target 220 using the graduation 232.

FIG. 4 shows the third embodiment of the screening device 300.

In this embodiment, the principal used to screen for a possible state of ophthalmic fatigue of the patient is the same as that used with the screening device 200 in FIG. 3.

The screening device 300 is in contrast binocular, and thus allows a possible state of fatigue of the patient to be detected either simultaneously or in succession in both eyes of the patient.

In this embodiment, the carrier 310 is on the whole the shape of a pair of binoculars. It more precisely has an overall parallelepipedal shape that is elongate along a longitudinal axis A3, with a top face 310A and a bottom face, two lateral faces 310B, and two end faces called the front face 310C and the back face.

The front face 310C of this carrier 310 is substantially flat. It has a width of about 18 centimeters and a height of about 7 centimeters. It is apertured with two rectangular windows 315 allowing the patient to see with his two eyes into the interior of the carrier 310. These windows 315 are here obstructed by transparent panes, in order to prevent dust infiltrating into the interior of the carrier 310.

In order to allow the patient to see the target 320, provision is made, in the interior of the carrier 310, for lighting means, here formed by the light-emitting diodes supplied with power by electrical batteries.

The bearing portion 311 of this carrier 310, which portion 311 is intended to be applied against the face or spectacles of the patient, is thus here formed by the front face 310C of this carrier 310. Provision is especially made for a hollow indent in the lower edge of the front face 310C, which forms a nose rest.

The slide rail 312 of this carrier 310, in which rail 312 the target 320 slides, is for its part formed by a rectilinear longitudinal slit that extends over only some of the length of the top face 310A of the carrier 310, parallel to the longitudinal axis A3. Here, this slide rail 312 opens neither onto the front face 310C nor onto the back face of the carrier 310.

The target 320 is identical to that shown in FIG. 2. It is positioned in the carrier 310 in such a way that it is simultaneously visible by both the eyes of the patient through the windows 315.

In this embodiment, two separate graduations 330 and 331 are provided, placed on either side of the slide rail 312.

Each graduation 330, 331 is borne by a rectangular sticker on which ages are printed. These two stickers are then adhesively bonded parallel to the slide rail 212, along the length of the latter.

As in the second embodiment of the screening device shown in FIG. 3, the scales of the ages printed on the two stickers are not the same.

It may thus be seen in FIG. 4 that one of the graduations 330 indicates ages comprised between 28 and 46 years, and that the other of the graduations 331 indicates ages comprised between 16 and 27 years.

Provision is thus made, in the interior of the carrier 310, for two scaling lenses (not shown in the figures) suitable for being engaged opposite the two windows 315 of the carrier 310 or for being disengaged from said windows 315, in order to allow one or other of the two graduations 330, 331 to be used.

The screening device 300 thus comprises means for manually moving these two scaling lenses, allowing them to be engaged or disengaged from the windows 315 of the carrier 310 independently of each other.

Here, these moving means are formed by two cursors 314 that are located on the top face 310A of the carrier 310, opposite the two windows 315, and that are movable between two positions in which they point toward one or other of two numbers denoted "1" and "2".

Thus, it will be understood that when the cursors 314 are placed on the number "1", the graduation to be used by the optician to position the target 320 is the graduation 330 (opposite which appears the inscription "1"), and that when the cursors 314 are placed on the number "2", the graduation to be used by the optician to position the target 320 is the graduation 331 (opposite which appears the inscription "2").

Provision is moreover made, in the interior of the carrier 310, for two masks (not shown in the figures) for masking one or other of the windows 315 when the optician desires to use the screening device 300 in succession on each eye of the patient and not simultaneously on both eyes of the patient.

The screening device 300 thus comprises means for manually moving these two masks, allowing them to be engaged or disengaged from the windows 315 of the carrier 310 independently of each other.

Here, these moving means are formed by two cursors 316 that are located on the two lateral faces 310B of the carrier 310, respectively, level in height with the two windows 315, and that are movable between two positions in which they point toward a black circle or toward a black disk.

Thus, it will be understood that when the cursors 316 are placed on the black disks, the windows 315 are obstructed, and that when the cursors 316 are placed on the black circles, the windows 315 are freed in order to leave the target 320 visible through the windows 315.

Provision is moreover made, in the interior of the carrier 310, for two corrective lenses of 0.6 diopters (not shown in the figures) suitable for being engaged opposite the two windows 315 of the carrier 310 or for being disengaged from said windows 315.

The screening device 300 thus comprises means for manually moving these two corrective lenses, allowing them to be engaged or disengaged from the windows 315 of the carrier 310 independently of each other.

Here, these moving means are formed by two cursors 313 that are located on the top face 310A of the carrier 310, opposite the two windows 315, and that are movable between two positions in which they point toward one or other of two symbols denoted "Ø" and "○".

Thus, it will be understood that when the cursors 313 are placed on the symbol "Ø", the corrective lenses are not located on the axis of the windows 315, whereas when the cursors 313 are placed on the symbol "○", the corrective lenses are located on the axis of the windows 315.

The way in which this screening device 300 is used is the same as that described above, the only difference being that it is now possible to carry out this screening either simultaneously or in succession on both the eyes of the patient.

In the case of simultaneous binocular screening of both eyes of the patient, provision will possibly be made for the corrective lenses to each have a nonzero prismatic power, in order to correct possible prismatic fatigue of the eyes.

FIG. 3 shows the fourth embodiment of the screening device 400.

In this embodiment, the screening device is formed by a simple tablet computer that comprises a casing 402, a touchscreen 401 engaged in the casing 402, means 410 for detecting the distance separating the touchscreen 402 from the face of the patient, and a central unit that is housed in the casing 402 and in which a diagnostic software package is stored in memory.

The detecting means 410, which could for example be formed by a simple video camera, are here formed by an ultrasound distance sensor.

Screening for a possible state of ophthalmic fatigue of the patient by means of this tablet 400 is then performed in the following way.

Beforehand, the patient starts the diagnostic software package and inputs his age. He moreover puts on his spectacles if he customarily wears such spectacles. He then separates the tablet 400 from his face until it is held at arm's-length.

By virtue of the detecting means 410, the diagnostic software package then acquires the distance separating the touchscreen 401 from the eyes of the patient.

The software package then commands the display on the touchscreen 401 of a message asking the patient to move the touchscreen 401 further away from or closer toward his eyes. The objective of this operation is for the distance separating the touchscreen 401 from the eyes of the patient to be equal to the distance $D_{age}$ (such as defined in the first embodiment of the invention).

The software package then commands the display on the touchscreen 401 of the letter "E", and of a message and two buttons in order to allow the patient to input the result of this examination, in order for the software package to acquire information as to whether or not the patient was able to read the displayed letter.

If he was able to read the displayed letter, the software package commands the display on the touchscreen 401 of a message indicating to the patient that he does not require a pair of antifatigue spectacles.

In contrast, if he was unable to read the displayed letter, a message asking the patient to move the touchscreen 401 further away from his eyes is displayed on the touchscreen 401. When the touchscreen 401 is sufficiently far away, the software package commands the display on the touchscreen 401 of an enlarged letter "E" 420 in order to check whether it is only a state of fatigue that is affecting the eyes of the wearer (and that this visual problem is not more serious).

The size of this letter "E" is calculated relative to the size of the letter "E" initially displayed in such a way that the letter "E" appears a constant size to the patient even though the touchscreen 401 is further away. A method of calculation allowing the letter "E" to appear to the patient to be a constant angular size is described in document U.S. Pat. No. 7,393,102.

Once more holding the tablet 400 at arm's-length, the patient then tries to read the letter "E" displayed on the touchscreen 401.

The software package then commands the display on the touchscreen 401 of a message and two buttons in order to allow the patient to input the result of this examination into the tablet 400, in order for the software package to acquire information as to whether or not the patient was able to read the letter displayed on the screen.

If he was able to read the displayed letter, the software package commands the display on the touchscreen 401 of a message indicating to the patient that he requires a pair of antifatigue spectacles.

In contrast, if he was unable to read the displayed letter, the software package commands the display on the touchscreen 401 of a message asking the patient to visit an optometrist for additional examinations.

The diagnostic software package of the tablet 400, if the latter is connected to a computer network, may then command a message to be sent to an optician providing the results of the measurement carried out.

The present invention is in no way limited to the embodiments described and shown, and those skilled in the art will be able to make modifications thereto without departing from the scope of the invention.

In particular, provision could be made for the size of the displayed letter "E" to be adjusted also depending on the time of day at which the screening is carried out, the eyes of the patient being naturally more fatigued in the evening than in the morning.

As yet another variant, provision could be made for a screening device such as that shown in the first embodiment, but devoid of transverse slit for receiving a corrective lens. Thus, when the patient is unable to read the letter "E" printed on the target, the optician, instead of using a corrective lens, rather draws back the target by a given distance in order to make the letter "E" easier to read, this distance for example corresponding to two years on the graduation.

Provision could also be made for the bearing portion of the screening device to be suitable for resting on the face of the patient, at a distance away from his eyes. The screening device will thus rest in the same way on the face of the patient, i.e. in the same position, whether or not the patient is wearing a pair of spectacles.

According to another variant of the invention (not shown in the figures) provision could be made for the corrective lens to be mounted on the carrier via a pivot, so as to be retractable. This lens would thus be movable between a position of use in which it would be located between the bearing portion and the target, and a retracted position in which it would be angularly offset by 90° relative to its position of use.

The invention claimed is:

1. A method for screening for a state of ophthalmic fatigue of an individual, comprising steps:
   a1) of positioning a target relative to the individual in such a way that the target is visible by at least one of the two eyes of the individual;
   a2) of appraisal by the individual of the clearness of the target; and
   a3) of deducing a state of ophthalmic fatigue of the individual depending on whether the target is seen clearly or hazily by the individual,
   said method for screening comprising, a step a0) of adjusting the size of the target or the position of the target relative to the individual, depending on the age of the individual, said step a0) being performed prior to step a2) and said step a0) being performed prior to or following step a1) and step a2).

2. The screening method as claimed in claim 1, in which if, in step a2), the target is seen to be hazy by the individual, provision is made following step a3) for steps:
   b1) of enlarging the size of the target or of moving the target away from the individual by a preset distance;
   b2) of appraisal by the individual of the clearness of the target; and
   b3) if, in step b2), the individual sees the target more clearly than in step a2), of deducing a need for an antifatigue correction.

3. The screening method as claimed in claim 2, in which, in step a0), only the distance between the target and the individual is adjusted.

4. The screening method as claimed in claim 3, in which step b1) consists in inserting at least one corrective lens between the eye of the individual and the target.

5. The screening method as claimed in claim 4, in which the corrective lens has a nonzero spherical power or a nonzero cylindrical power or a nonzero prismatic power or an antireflection coating or a tinted coating or is formed by a lens with a depth of field.

6. The screening method as claimed in claim 2, in which, in step a0), only the size of the target is adjusted.

7. The screening method as claimed in claim 6, in which step b1) consists in enlarging the size of the target.

8. The screening method as claimed in claim 1, in which, in step a0), the size of the target or the position of the target relative to the individual are/is adjusted also depending on the time of day at which the screening is carried out or on the geographical origin of the individual or on the clearness of the target or on the contrast of the target.

9. The screening method as claimed in claim 1, in which, prior to step a2), the individual is equipped with his customary corrective equipment.

10. The screening method as claimed in claim 1, in which steps a1) and a2) are carried out simultaneously or in succession on both eyes of the individual.

11. The screening method as claimed in claim 1, in which, following step a3), provision is made for a step c1) of storing the state of ophthalmic fatigue deduced in step a3) in memory and of transmitting said state to a remote location.

12. A device for screening for a state of ophthalmic fatigue of an individual, comprising:
   a carrier comprising a bearing portion to be applied against the face or against the spectacles of an individual and a slide rail;
   a target slidably mounted in the slide rail of the carrier; and
   at least one graduation located along the slide rail for pinpointing the position of the target in the slide rail,
   wherein said graduation indicates ages and the carrier comprises positioning means, located between the bearing portion and the target, that are suitable if required for receiving any corrective lens so that the corrective lens remains removable in order if required to make it easier to see the target.

13. The screening device as claimed in claim 12, in which provision is made for at least two age-indicating graduations and in which provision is made for means for positioning a scale-changing lens, said means being located between the bearing portion and the target.

14. The screening device as claimed in claim 12, in which the target (120; 220; 320) comprises at least one letter or image.

* * * * *